(12) United States Patent
Nielsen et al.

(10) Patent No.: US 10,575,772 B2
(45) Date of Patent: Mar. 3, 2020

(54) SYSTEM, APPARATUS AND METHOD FOR MEASUREMENT OF MUSCLE STIFFNESS

(71) Applicants: Movotec A/S, Charlottenlund (DK); Københavns Universitet, København K (DK)

(72) Inventors: Jens Bo Nielsen, Virum (DK); Johnny Erik Westergaard, Stenløse (DK); Peder Esben Bilde, Frederiksberg C (DK)

(73) Assignees: Movotec A/S, Charlottenlund (DK); Københavns Universitet, Københaven K (DK)

( * ) Notice: Subject to any disclaimer, the term of this patent is extended or adjusted under 35 U.S.C. 154(b) by 388 days.

(21) Appl. No.: 15/125,088

(22) PCT Filed: Mar. 11, 2015

(86) PCT No.: PCT/EP2015/055054
§ 371 (c)(1),
(2) Date: Sep. 9, 2016

(87) PCT Pub. No.: WO2015/135981
PCT Pub. Date: Sep. 17, 2015

(65) Prior Publication Data
US 2017/0020437 A1    Jan. 26, 2017

(30) Foreign Application Priority Data
Mar. 12, 2014  (EP) .................................. 14159223

(51) Int. Cl.
*A61B 5/11* (2006.01)
*A61B 5/00* (2006.01)
*A61B 5/0488* (2006.01)

(52) U.S. Cl.
CPC .......... *A61B 5/4519* (2013.01); *A61B 5/0488* (2013.01); *A61B 5/1107* (2013.01);
(Continued)

(58) Field of Classification Search
CPC ... A61B 5/4519; A61B 5/7278; A61B 5/0488; A61B 5/1122; A61B 5/1107; A61B 2562/0219
See application file for complete search history.

(56) References Cited

U.S. PATENT DOCUMENTS 4,905,676 A * 3/1990 Bond ..................... A63B 24/00
                                                           601/34
6,063,044 A * 5/2000 Leonard ............... A61B 5/0053
                                                          600/587
(Continued)

FOREIGN PATENT DOCUMENTS

JP    S 61206431 A    9/1986
JP    S 63318928 A    12/1988
(Continued)

OTHER PUBLICATIONS

Doemges, F. and Rack, P. M. H., Changes in the Stretch Reflex . . . . Different Tasks, 1992, Journal of Physiology, pp. 563-573.*
(Continued)

*Primary Examiner* — Daniel L Cerioni
*Assistant Examiner* — Raymond P Dulman
(74) *Attorney, Agent, or Firm* — Knobbe Martens Olson & Bear, LLP

(57) ABSTRACT

A system, an apparatus, and a method for measuring muscle stiffness in a predetermined joint of an individual are provided. The system and apparatus comprises a measuring unit and a processing unit. The measuring unit is configured to be applied to a body segment of the predetermined joint. The processing unit is configured to: receive a plurality of data
(Continued)

sets from the at least one measurement device, analyze the plurality of data sets for one or more indications of an elicited stretch reflex, and calculate a muscle stiffness score. The muscle stiffness score is based on at least a difference between a first stiffness and a second stiffness. The first stiffness is determined from the first subset, and the second stiffness is determined from the second subset.

17 Claims, 9 Drawing Sheets

(52) U.S. Cl.
CPC .......... *A61B 5/1122* (2013.01); *A61B 5/6831* (2013.01); *A61B 5/7278* (2013.01); *A61B 2562/0219* (2013.01)

(56) References Cited

U.S. PATENT DOCUMENTS

| | | | | |
|---|---|---|---|---|
| 2003/0135129 | A1* | 7/2003 | Cusimano | A61B 5/0488 600/546 |
| 2006/0052729 | A1* | 3/2006 | Gurses | A61B 5/0053 601/46 |
| 2006/0167564 | A1* | 7/2006 | Flaherty | A61B 5/0476 623/57 |
| 2007/0027631 | A1* | 2/2007 | Cabrera | A61B 5/1107 702/19 |
| 2007/0172797 | A1* | 7/2007 | Hada | G09B 23/32 434/1 |
| 2008/0077057 | A1* | 3/2008 | Peles | A61H 1/0277 601/5 |
| 2008/0119763 | A1* | 5/2008 | Wiener | A61B 5/224 600/587 |
| 2008/0221487 | A1* | 9/2008 | Zohar | A61B 5/103 600/595 |
| 2010/0130893 | A1* | 5/2010 | Sankai | A61B 5/1071 601/5 |
| 2010/0152619 | A1* | 6/2010 | Kalpaxis | A61B 5/0002 600/592 |
| 2011/0196262 | A1* | 8/2011 | McLeod | A61B 5/0053 600/587 |
| 2011/0201904 | A1* | 8/2011 | Cusimano Reaston | A61B 5/00 600/301 |
| 2011/0208444 | A1* | 8/2011 | Solinsky | A61B 5/112 702/41 |
| 2011/0251021 | A1* | 10/2011 | Zavadsky | A63B 21/00 482/5 |
| 2013/0053731 | A1* | 2/2013 | Sakoda | A61B 5/1071 600/587 |
| 2013/0204545 | A1* | 8/2013 | Solinsky | G01P 13/00 702/44 |
| 2013/0211259 | A1* | 8/2013 | Komistek | A61B 8/5223 600/440 |

FOREIGN PATENT DOCUMENTS

| | | |
|---|---|---|
| WO | WO 2006/102764 A1 | 10/2006 |
| WO | WO 2008/121067 | 10/2008 |
| WO | WO 2008/121067 A1 | 10/2008 |

OTHER PUBLICATIONS

Ansari, Noureddin Nakhostin et al., "The Modified Tardieu Scale for the measurement of elbow flexor spasticity in adult patients with hemiplegia" Brain Injury, Dec. 2008, pp. 1007-1012, vol. 22, Issue 13-14.

Ansari, Noureddin Nakhostin et al., "Development of the Persian version of the Modified Modified Ashworth Scale: translation, adaptation, and examination of interrater and intrarater reliability in patients with poststroke elbow flexor spasticity" Disability & Rehabilitation, 2012; pp. 1843-1847, vol. 34, No. 21.

Biering-Sørensen, F. et al., "Spasticity-assessment: a review" Spinal Cord, 2006, pp. 708-722, vol. 44.

Lorentzen, Jakob et al., "Distinguishing active from passive components of ankle plantar flexor stiffness in stroke, spinal cord injury and multiple sclerosis" Clinical Neurophysiology, 2010.

Willerslev-Olsen, Maria et al., "Passive muscle properties are altered in children with cerebral palsy before the age of 3 years and are difficult to distinguish clinically from spasticity" Developmental Medicine & Child Neurology, 2013, pp. 617-623, vol. 55.

European Search Report for EP 14159223 dated Aug. 15, 2014.

International Search Report for PCT/EP2015/055054 dated Jun. 15, 2015.

* cited by examiner

SYSTEM, APPARATUS AND METHOD FOR MEASUREMENT OF MUSCLE STIFFNESS

The present invention relates to a method and a device for measuring muscle stiffness, especially for measuring muscle stiffness in individuals suffering from cerebral palsy.

BACKGROUND

Cerebral palsy (CP) is the most common childhood motor disability. It is caused by a brain lesion before or immediately after birth. It is often described as an "umbrella term" comprising several different syndromes. CP is considered as one of the most severe disabilities in childhood and has a strong impact on families and children themselves. Moreover cerebral palsy makes heavy demands on health, education and social services. The life expectancy of children with cerebral palsy is increasing worldwide, even among children with a severe level of impairment.

The majority of children with CP develop muscle spasticity early in childhood which may impact their ability of performing voluntary movement. Furthermore, muscular changes that greatly interfere with movement typically develop early and may result in joint deformities and reduced range of movement. These changes usually require surgical intervention at some point during childhood to improve joint mobility.

Spasticity is also commonly associated with other disorders or injuries such as spinal cord injury, multiple sclerosis, stroke and traumatic brain injuries.

For assessment of muscle spasticity two subjective scales (and methods) are normally used: The Modified Ashworth Scale (MAS) and the Modified Tardieu Scale (MTS). None of them are known to be objective and sufficiently reliable. Since the diagnosis and the following treatment are mainly or partly based on these scales there is a risk of wrong treatment. Studies conclude that there is a need of simple instruments, which provide a reliable quantitative measure with a low inter-rater variability.

WO 2008/121067 discloses a system to evaluate spasticity in a movable extremity, wherein a joint is passively extended at two constant velocities, slow and fast. The slow velocity movement is performed without any reflex contribution, and the fast velocity movement is performed with reflex contribution.

WO 2006/102764 discloses a method for measurement of spasticity in a patient by recording an EMG signal while the limb is being moved at a variety of angular velocities.

US 2007/027631 discloses an apparatus and a method for evaluating spasticity in a movable extremity. The apparatus includes an accelerometer, a gyroscope, and a sensor adapted for quantifying force or pressure. The method includes moving the extremity through a range of motion about an axis of rotation. Measured parameters are transmitted to a data processor which processes the data to generate information that characterizes the hypertonic condition.

SUMMARY

The present invention provides a system, an apparatus, and a method which provides objective and reproducible measurement of a muscle stiffness score indicative of the muscle spasticity. Furthermore the present invention provides a system, an apparatus, and a method which in calculation of the muscle stiffness score distinguishes the passive and active components of muscle stiffness, and hence may reduce the risk of wrong diagnosis and treatment.

Accordingly, a system for measuring muscle stiffness in a predetermined joint of an individual is provided. The system comprises a measuring unit and a processing unit. The measuring unit is configured to be applied to a body segment of the predetermined joint. The measuring unit comprises a housing and at least one measurement device comprising a force transducer. The processing unit is configured to: receive a plurality of data sets from the at least one measurement device, analyze the plurality of data sets for one or more indications of an elicited stretch reflex, e.g. based on the measurement data, and calculate a muscle stiffness score.

The one or more indications of an elicited stretch reflex may comprise indications such as increased muscular activity, increased applied force, a reversal of angular velocity, or any combination hereof.

The plurality of data sets may comprise measurement data measured during any number of trials, such as a plurality of trials. The trials may be a set of movements of the body segment. The trials may for example comprise moving the body segment with an angular velocity and/or a plurality of angular velocities, by applying external force to the body segment via the measuring unit, such as an examiner applying external force to the body segment via the measuring unit. The measurement data may comprise applied force data. The applied force data may be indicative of the external force applied to the body segment by the examiner.

A first subset and a second subset of the plurality of data sets may be determined, e.g. by analyzing the plurality of data sets for one or more indications of an elicited stretch reflex. The first subset may comprise data sets in which at least one of the one or more indications of an elicited stretch reflex is present. The second subset may comprise data sets in which none of the one or more indications of an elicited stretch reflex is present.

The muscle stiffness score may be based on at least a difference between a first stiffness and a second stiffness. The first stiffness may be based on applied force data and determined from the first subset. The second stiffness may be based on applied force data and determined from the second subset.

The first and/or second stiffness may be determined from e.g. an average, median and/or sum of calculated stiffnesses of data sets in the respective subset.

The body segment for which the measuring unit is configured to be applied may be a body segment distal to the predetermined joint.

In a further aspect, a muscle stiffness apparatus for measuring muscle stiffness in a predetermined joint of an individual is provided. The muscle stiffness apparatus is configured to be applied to a body segment of the predetermined joint. The muscle stiffness apparatus comprises a housing, at least one measurement device comprising a force transducer, and a processing unit. The processing unit is configured to: receive a plurality of data sets from the at least one measurement device, analyze the plurality of data sets for one or more indications of an elicited stretch reflex, e.g. based on the measurement data, and calculate a muscle stiffness score.

The one or more indications of an elicited stretch reflex may comprise indications such as increased muscular activity, increased applied force, a reversal of angular velocity, and/or any combination hereof.

The plurality of data sets may comprise measurement data measured during any number of trials, such as a plurality of trials. The trials may be a set of movements of the body segment. The trials may for example comprise moving the body segment with an angular velocity and/or a plurality of angular velocities, by applying external force to the body segment via the measuring unit, such as an examiner applying external force to the body segment via the measuring unit. The measurement data may comprise applied force data. The applied force data may be indicative of the external force applied to the body segment by the examiner.

A first subset and a second subset of the plurality of data sets may be determined, e.g. by analyzing the plurality of data sets for one or more indications of an elicited stretch reflex. The first subset may comprise data sets in which at least one of the one or more indications of an elicited stretch reflex is present. The second subset may comprise data sets in which none of the one or more indications of an elicited stretch reflex is present.

The muscle stiffness score may be based on at least a difference between a first stiffness and a second stiffness. The first stiffness may be based on applied force data and determined from the first subset. The second stiffness may be based on applied force data and determined from the second subset.

The first and or second stiffness may be determined from e.g. an average, median and/or sum of calculated stiffnesses of data sets in the respective subset.

The body segment for which the muscle stiffness apparatus is configured to be applied may be a body segment distal to the predetermined joint.

In a further aspect, a method for calculating a muscle stiffness score is provided. The method comprises: receiving a plurality of data sets comprising measurement data, analyzing the plurality of data sets for one or more indications of an elicited stretch reflex, e.g. based on the measurement data, and calculating a muscle stiffness score.

The one or more indications of an elicited stretch reflex may comprise indications such as increased muscular activity, increased applied force, a reversal of angular velocity, and/or any combination hereof.

The measurement data may be obtained by moving a body segment with an angular velocity by applying external force to the body segment.

The measurement data may be measured during a plurality of trials. The plurality of trials may comprise moving a body segment with an angular velocity, and/or a plurality of angular velocities, by applying external force to the body segment, such as an examiner applying external force to the body segment via the measuring unit. The measurement data may comprise applied force data. The applied force data may be indicative of the external force applied to the body segment by the examiner.

Analyzing the plurality of data sets may comprise determining a first subset and a second subset of the plurality of data sets. The first subset may comprise data sets in which at least one of the one or more indications of an elicited stretch reflex is present.

The second subset may comprise data sets in which none of the one or more indications of an elicited stretch reflex is present.

Calculating the muscle stiffness score may be based on at least a difference between a first stiffness and a second stiffness. The first stiffness may be based on applied force data and determined from the first subset. The second stiffness may be based on applied force data and determined from the second subset.

In a further aspect, a method for calculating a muscle stiffness score in a predetermined joint of an individual is provided. The method comprising that at least one measurement device is applied to a body segment of the predetermined joint, and any number of trials, such as a plurality of trials, is performed. The trials comprise moving the body segment with an angular velocity, and/or a plurality of angular velocities, by applying external force to the body segment, such as an examiner applying external force to the body segment via the measuring unit. The method further comprises: receiving a plurality of data sets from the at least one measurement device, analyzing the plurality of data sets for one or more indications of an elicited stretch reflex, e.g. based on the measurement data, and calculating the muscle stiffness score.

The one or more indications of an elicited stretch reflex may comprise indications such as increased muscular activity, increased applied force, a reversal of angular velocity, and/or any combination hereof.

The plurality of data sets may comprise measurement data measured during any number of trials, such as a plurality of trials. The trials may be a set of movements of the body segment. The trials may comprise moving the body segment with an angular velocity and/or a plurality of angular velocities by applying external force to the body segment via the measuring unit, such as an examiner applying external force to the body segment via the measuring unit.

A first subset and a second subset of the plurality of data sets may be determined, e.g. by analyzing the plurality of data sets for one or more indications of an elicited stretch reflex. The first subset may comprise data sets in which at least one of the one or more indications of an elicited stretch reflex is present. The second subset may comprise data sets in which none of the one or more indications of an elicited stretch reflex is present.

The muscle stiffness score may be based on at least a difference between a first stiffness and a second stiffness. The first stiffness may be determined from the first subset. The second stiffness may be determined from the second subset.

The body segment for applying at least one measurement device may be a body segment distal to the predetermined joint.

It is an advantage of the present disclosure that a muscle stiffness score may be assessed in an alternative and better way. Thus potentially unnecessary treatments may be avoided or reduced and correct treatments may be initiated at an earlier stage.

It is a further advantage of the present disclosure that the resulting muscle stiffness score may be less dependent on a subjective assessment of an examiner, thereby resulting in more reliable and consistent examinations. Furthermore, this may lead to an improved possibility of detecting improvements in a patient's condition.

It is a further advantage of the present disclosure that trials may be analyzed to determine whether a reflex has been elicited or not, contrary to relying on predetermined fast and slow movements, such as in WO 2008/121067. It should be noted that the precise velocity threshold for eliciting a reflex is not necessarily known as this threshold is different between individuals.

Thus determining whether or not a reflex has been elicited, based on the measurement data further provides that any velocities of movements may be used, e.g. including velocities which are not distinctively fast or slow, such as non-constant or changing velocities. Thereby, a more user friendly method and/or apparatus and/or system is provided.

It is a further advantage of the present disclosure that a quantifiable muscle stiffness score is provided. Whereas prior art, such as WO 2006/102764, only rely on EMG as a measurement which fails to provide an examiner with quantifiable information pertaining to the stiffness of the joint.

It is a further advantage of the present disclosure that the apparatus and/or system may be provided as a handheld device, which may allow easy assessment of muscle stiffness in a non-hospital environment, such as in a private home.

It is a further advantage of the present disclosure that the method, the apparatus, and/or the system may rely on substantially rigid parts for measuring. Thereby, a device less subject to mechanical failure may be provided, and increased user-friendliness may be obtained.

Muscle stiffness is a measure of the resistance against a movement of a joint. This resistance may primarily be caused by the muscle(s) of the joint resisting to be stretched. Hence, muscle stiffness may be measured for a joint.

It is an advantage of the present invention that it is possible to distinguish between passive stiffness and active stiffness whereas known methods such as Modified Ashworth Scale (MAS) and the Modified Tardieu Scale (MTS), besides being subjective and not sufficiently reliable, provide a common score of spasticity and thus do not distinguish between passive stiffness and active stiffness. A method such as disclosed by US 2007/027631 similarly does not provide separation between stiffnesses in situations wherein a stretch reflex was elicited, and in situations in which a stretch reflex was not elicited.

Spasticity is a velocity-dependent increase in muscle tone caused by hyperactive stretch reflexes, which occurs when the affected muscle is stretched. This reflex mediated increase in muscle tone (active stiffness) may be confused with changes in the elastic properties of the muscles (passive stiffness).

The passive stiffness is significantly increased in CP patients compared to non CP patients due to higher muscle contractures whereas the active stiffness is often normal. Similar findings for adults with spinal cord injuries, stroke or multiple sclerosis have been shown.

It is a further advantage of the present invention that by being able to distinguish between active stiffness and passive stiffness it may be avoided that anti-spastic medicine is used unnecessarily, in that the passive stiffness most often cannot be altered with anti-spastic medicine like Botulium Toxin, Baclofen or other as such medicine typically has only effect on neurologic reflex mediated activities.

The method may be implemented with the system for measuring muscle stiffness or the muscle stiffness apparatus as also provided. At least a part of the method may be incorporated in software adapted to run in a processing unit, such as the processing unit of the system for measuring muscle stiffness or the processing unit of the muscle stiffness apparatus.

The plurality of data sets are divided into subsets, such as into two, three, four subsets, typically into two subsets, such as a first subset and a second subset. The determination of which of the plurality of data sets is allocated to which subset is determined based on the one or more indications of an elicited stretch reflex. Data sets, in which at least one of the one or more indications of an elicited stretch reflex is present, are allocated to the first subset. The second subset may comprise data sets in which none of the one or more indications of an elicited stretch reflex is present.

In practice, some data sets may be discarded, e.g. due to measurement errors, noise, or other failure to meet a minimum quality standard. The plurality of data sets may under these circumstances denote the plurality of data sets which are not discarded.

The plurality of data sets are received from the at least one measurement device. The plurality of data sets may be received one by one, and stored in a memory, e.g. a first data set is received after a first trial, a second data set is received after a second trial, a third data set is received after a third trial, etc. Alternatively, the plurality of data sets may be collected in a memory of the at least one measurement device and subsequently, the plurality of data sets may be received collectively from the at least one measurement device.

The at least one measurement device may comprise one or more accelerometers. The measurement data may comprise acceleration data, such as acceleration data from the one or more accelerometers. The at least one measurement device may comprise one or more gyroscopes. The measurement data may comprise angular velocity data, such as angular velocity data from the one or more gyroscopes. The measurement data may comprise information of an angle and/or an angular displacement, e.g. a total angular displacement. An angle, and/or an angular displacement may be calculated from angular velocity data.

The one or more accelerometers and/or the one or more gyroscopes may provide information on the orientation and/or motion of the measuring unit, e.g. acceleration data and/or angular velocity data. Information of the orientation and/or motion of the measuring unit may be used to determine a joint center of the predetermined joint. The joint center is considered the point and/or axis of rotation in the predetermined joint. Furthermore, information of the orientation and/or motion of the measuring unit may be used to determine the angular velocity of the rotation in the predetermined joint during movement of the body segment.

The housing may enclose the at least one measurement device, and the housing may comprise means for fixating the housing and hence the measurement device(s) to the body segment. Thereby, the measurement data, especially acceleration and angular velocity data, may provide a more precise measure of the actual movements of the body segment.

In some embodiments, a distance from the joint center to a defined position of the measuring unit may be determined automatically by the measuring unit and/or by the processing unit. Additionally or alternatively, the distance from the joint center to a defined position of the measuring unit may be measured manually, and entered into the processing unit via a user interface connected to the processing unit.

A stiffness, such as the first stiffness and/or the second stiffness may be based on the distance. For example, the distance may be used to calculate torque based on applied force data, i.e. torque data may be based on the distance and applied force data.

Stiffness, such as the first stiffness and/or the second stiffness, may be calculated as torque divided by an angle, e.g. an angular displacement.

The processing unit may calculate acceleration and angular velocity of the measuring unit, such as relative to a reference point, e.g. the predetermined joint and/or the joint center, based on measurements received from the one or more accelerometer(s) and the one or more gyroscope(s), such as acceleration data from the one or more accelerometer(s) and/or angular velocity data from the one or more gyroscope(s).

The at least one measurement device may comprise a plurality of accelerometers, such as two accelerometers, such as a first accelerometer and a second accelerometer. The provision of two accelerometers may be beneficial to improve the accuracy of determining the joint center.

The provision of a combination of one or more accelerometer and one or more gyroscopes may provide more accurate measurements of both slow and fast movements.

The at least one measurement device may comprise one or more force transducers. The one or more force transducers may measure the external force applied to the body segment during movement of the body segment. The one or more force transducers may measure the external force applied to the body segment in three dimensions, such as to measure a resultant external force.

At least one of the one or more force transducers may be a tri-axial force transducer. Alternatively, the one or more force transducer may comprise a plurality of force transducers, e.g. two or three force transducers, positioned to measure the external force applied in a plurality of directions, e.g. two or three directions, such as in three perpendicular directions, such as three dimensions.

The at least one measurement device may comprise one or more torque transducers. The one or more torque transducers may measure the external torque applied to the body segment during movement of the body segment. The one or more torque transducers may measure the external torque applied to the body segment in two or three dimensions.

At least one of the one or more torque transducers may be a tri-axial torque transducer. Alternatively the one or more torque transducers may comprise a plurality of torque transducers, e.g. two or three torque transducers, positioned to measure the external torque applied in a plurality of directions, e.g. two or three directions, such as three perpendicular directions, such as three dimensions.

The at least one measurement device may comprise a combined torque and force transducer, e.g. a multi-axial force and torque transducer or a six-axial force and torque transducer. A multi-axial or a six-axial force and torque transducer may be able to measure all components of force and torque in all three dimensions.

The measurement data may comprise applied force data, such as external force applied measured by the one or more force transducers and/or the one or more torque transducers.

The measuring unit may comprise a handle. The handle may extend from inside the housing to outside the housing. The one or more force transducers may be configured for measuring force applied to the handle.

The measurement data may comprise applied torque data. The applied torque data may be calculated from measurement of applied force, such as applied force measured by the one or more force transducer and/or the one or more torque transducer.

The at least one measurement device may comprise one or more muscular activity detection units. The one or more muscular activity detection units may comprise an electromyography unit or a mechanomyography unit. A muscular activity detection unit may detect the muscular activity of a muscle adjacent to the predetermined joint. The measurement data may comprise muscular activity data, such as muscular activity data measured by the one or more muscular activity detection units. The muscular activity data may comprise muscular activity data of one muscle or a plurality of muscles.

The muscular activity unit may comprise surface electrode(s) and/or microphone(s) which may be positioned on the skin above a muscle for which the activity should be detected. The surface electrode(s) and/or the microphone(s) may be positioned on the skin above the muscle belly. Alternatively, or additionally, the muscular activity unit may comprise intramuscular electrodes which may, by penetration of the skin, be positioned in the muscle for which the activity should be detected.

The at least one measurement device may comprise a plurality of muscular activity detection units. A plurality of muscular activity units may provide a possibility to detect activity of a plurality of muscles and/or to incorporate different muscular activity detection methods e.g. electromyography and mechanomyography. A plurality of muscular activity units may also provide for a more precise measurement of muscular activity. The plurality of muscular activity units may comprise one or more electromyography units and/or one or more mechanomyography units.

Indications of an elicited stretch reflex may be seen on one or more measurements. For example, indications of an elicited stretch reflex may include one or more of, a sudden increase in the applied force, a sudden increase in the muscular activity, and/or a sudden decrease, or maybe even negative, angular velocity. Hence, analyzing the plurality of data sets may comprise analyzing applied force data of the plurality of data sets. Alternatively or additionally, analyzing the plurality of data sets may comprise analyzing muscular activity data of the plurality of data sets. Alternatively or additionally, analyzing the plurality of data sets may comprise analyzing angular velocity data of the plurality of data sets.

The plurality of data sets may comprise a trial data set. The processing unit may further be configured to receive the trial data set and/or analyze the trial data set for the one or more indications of an elicited stretch reflex. For example, the processing unit may receive a data set of a first trial; analyze the data set of the first trial before proceeding to receive a data set of a second trial. The processing unit may be configured to output a first signal if analysis of the trial data set comprises at least one of the one or more indications of an elicited stretch reflex, e.g. the processing unit may be configured to output the first signal if the trial data set comprises at least one of the one or more indications of an elicited stretch reflex. An examiner conducting the measuring of muscle stiffness may thus be notified as to whether the trial performed comprised one or more indications of an elicited stretch reflex. Similarly, the processing unit may be configured to output a second signal if analysis of the trial data set comprises none of the one or more indications of an elicited stretch reflex. The examiner may thus be notified whether the trial performed did not comprise one or more indications of an elicited stretch reflex.

In some embodiments, a signal, e.g. the first signal, may be provided if the trial data set comprises an indication of an elicited stretch reflex. In other embodiments, a signal, such as the second signal, may be provided if the trial data set does not comprise an indication of an elicited stretch reflex. In still further embodiments, a signal, such as the first signal, may be provided if the trial data set comprises an indication of an elicited stretch reflex and a signal, e.g. the second signal, may be provided if the trial data set does not comprise an indication of an elicited stretch reflex.

The measuring unit may be adapted to communicate with an additional device comprising the processing unit. For example, the additional device may be a computing device, such as a personal computer, a smartphone, a tablet computer etc.

Communication between the processing unit and the measuring unit may be performed by establishing a wireless or wired connection between the measuring unit and the processing unit, for example by establishing a USB wired connection, or the additional device may comprise a docking station, and the measuring unit may connect to the processing unit when inserted in the docking station. Alternatively, or as a supplement, the communication between the measuring unit and the additional device may be wirelessly, e.g. the measurement data may be wirelessly transmitted to the additional device. Hence, the measuring unit may comprise a wireless transceiver for wirelessly communicating with the additional device.

The measuring unit and/or the muscle stiffness apparatus may avoid movable connections between parts on each side of the predetermined joint. The measuring unit and/or the muscle stiffness apparatus may be configured to be applied only to one body segment, such as the body segment, of the predetermined joint.

The housing of the measuring unit and/or the muscle stiffness apparatus may comprise, such as enclose, the at least one measurement device. The housing may be a rigid housing. Thus, the at least one measurement device(s) may avoid dependence on movable parts such as hinges, springs etc.

The measuring unit may comprise a power supply and/or a battery for powering the components of the measuring unit, such as the at least one measurements device.

In some embodiments the measuring unit may comprise the processing unit. For example, the housing of the measuring unit may comprise the processing unit. The housing of the muscle stiffness apparatus may comprise the processing unit.

The measuring unit and/or the muscle stiffness apparatus may be a handheld device. The measuring unit, and/or the muscle stiffness apparatus, and/or the housing may have dimensions, e.g. length, width, and/or height, of less than 30 cm, such as less than 20 cm, such as less than 15 cm.

The number of trials may be performed with a variation of angular velocity, such as to elicit a stretch reflex in some trials and to not elicit a stretch reflex in other trials. Hence the angular velocity may comprise at least a plurality of angular velocities including a first angular velocity and a second angular velocity. The first angular velocity may be considered slow movements, e.g. angular velocities below 40 deg/s, such as angular velocities below 30 deg/s, such as angular velocities below 20 deg/s, such as angular velocities between 5 deg/s and 40 deg/s, such as between 10 deg/s and 30 deg/s, such as between 10 and 20 deg/s. The second angular velocity may be considered fast movements, e.g. angular velocities above 160 deg/s, such as angular velocities above 180 deg/s, such as angular velocities above 200 deg/s, such as angular velocities between 160 deg/s and 240 deg/s, such as between 180 deg/s and 220 deg/s.

Performance of the trials may comprise performing a first number of trials with slow movements and a second number of trials with a fast movement. Alternatively, the performance of the trials may comprise performing a number of trials wherein the angular velocity is varied conveniently, randomly or pseudo-randomly, between trials.

The result of the calculated stiffness score may be provided to an examiner. The muscle stiffness apparatus and/or the system may comprise an output unit. The output unit may be configured for presenting at least the calculated stiffness score. The output unit may be such as a visual display, a PC screen, a tablet computer, a smartphone etc.

The muscle stiffness score is an intermediate finding which in combination with other possible findings may aid an examiner in examining a patient. As an alternative term for "muscle stiffness score", as used in the present disclosure, the word "spasticity score" may be used. Hence, "muscle stiffness score" and "spasticity score" may be used interchangably for referring to the same score.

It is envisaged that any embodiments or elements as described in connection with any one aspect may be used with any other aspects or embodiments, mutatis mutandis. For example, the processing unit of the system and/or of the muscle stiffness apparatus may be configured to perform the method and/or parts of the method disclosed.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Like elements will, thus, not be described in detail with respect to the description of each figure.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
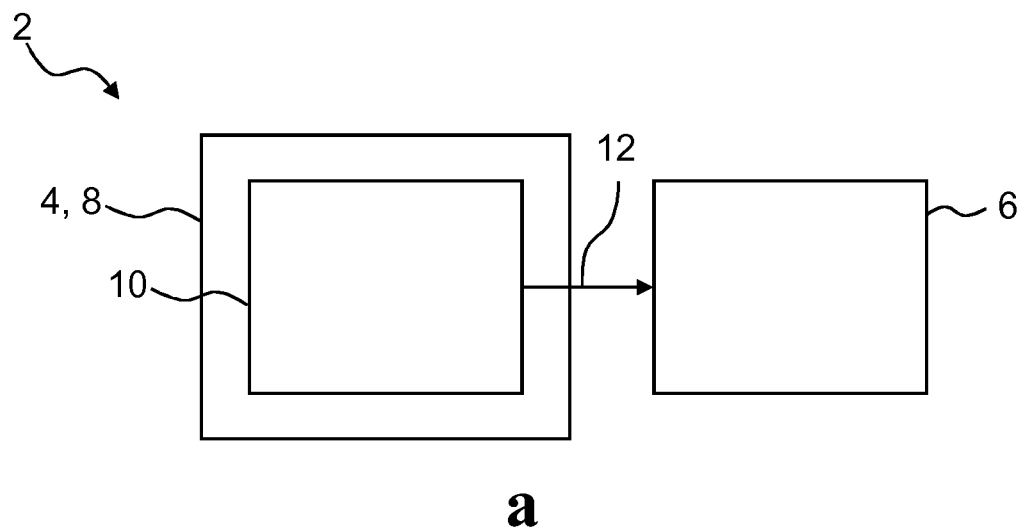
FIG. 1 schematically illustrates an exemplary system for measuring muscle stiffness, FIG. 2 schematically illustrates an exemplary system for measuring muscle stiffness, FIG. 3 schematically illustrates an exemplary measuring unit, FIG. 4 schematically illustrates an exemplary muscle stiffness apparatus for measuring muscle stiffness.
Figure 1:
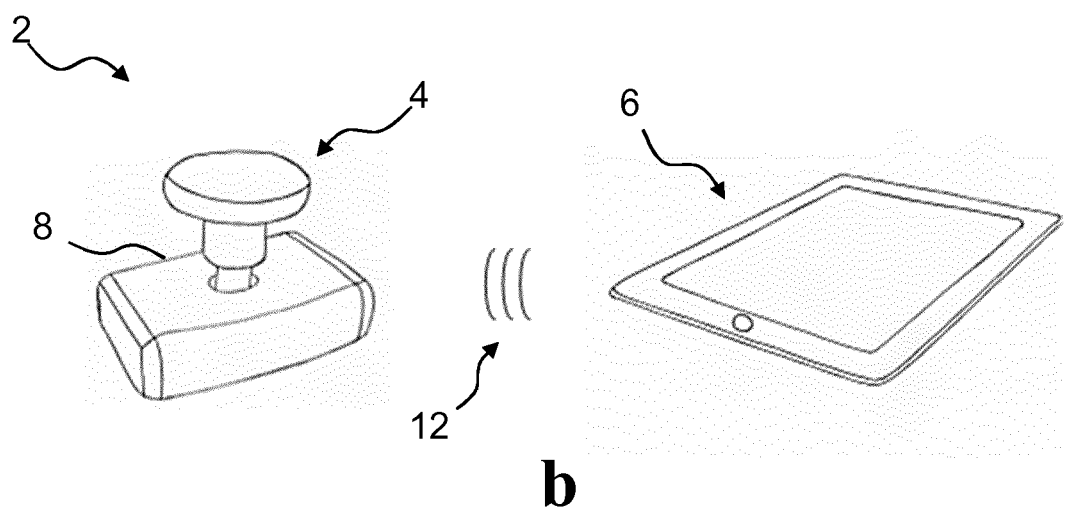

The figures are schematic and simplified for clarity, and they merely show details which are necessary for the understanding of the invention, while other details have been left out. Throughout, the same reference numerals are used for identical or corresponding parts.

FIG. 1a schematically shows an exemplary system 2 for measuring muscle stiffness in a subject (not shown). The system 2 comprises a measuring unit 4 and a processing unit 6. The measuring unit 4 comprises a housing 8 and a measurement device 10, and the measuring unit 4 is configured to be applied to a body segment e.g. a foot, a lower leg, or a forearm of the subject. As shown in FIG. 1a, the housing may comprise the measurement device 10.

FIG. 1b shows an exemplary embodiment of the exemplary system 2 as schematically illustrated in FIG. 1a.

The measuring unit 4 is configured to be applied to the body segment distal to the joint for which the muscle stiffness is to be measured.

Figure 9:
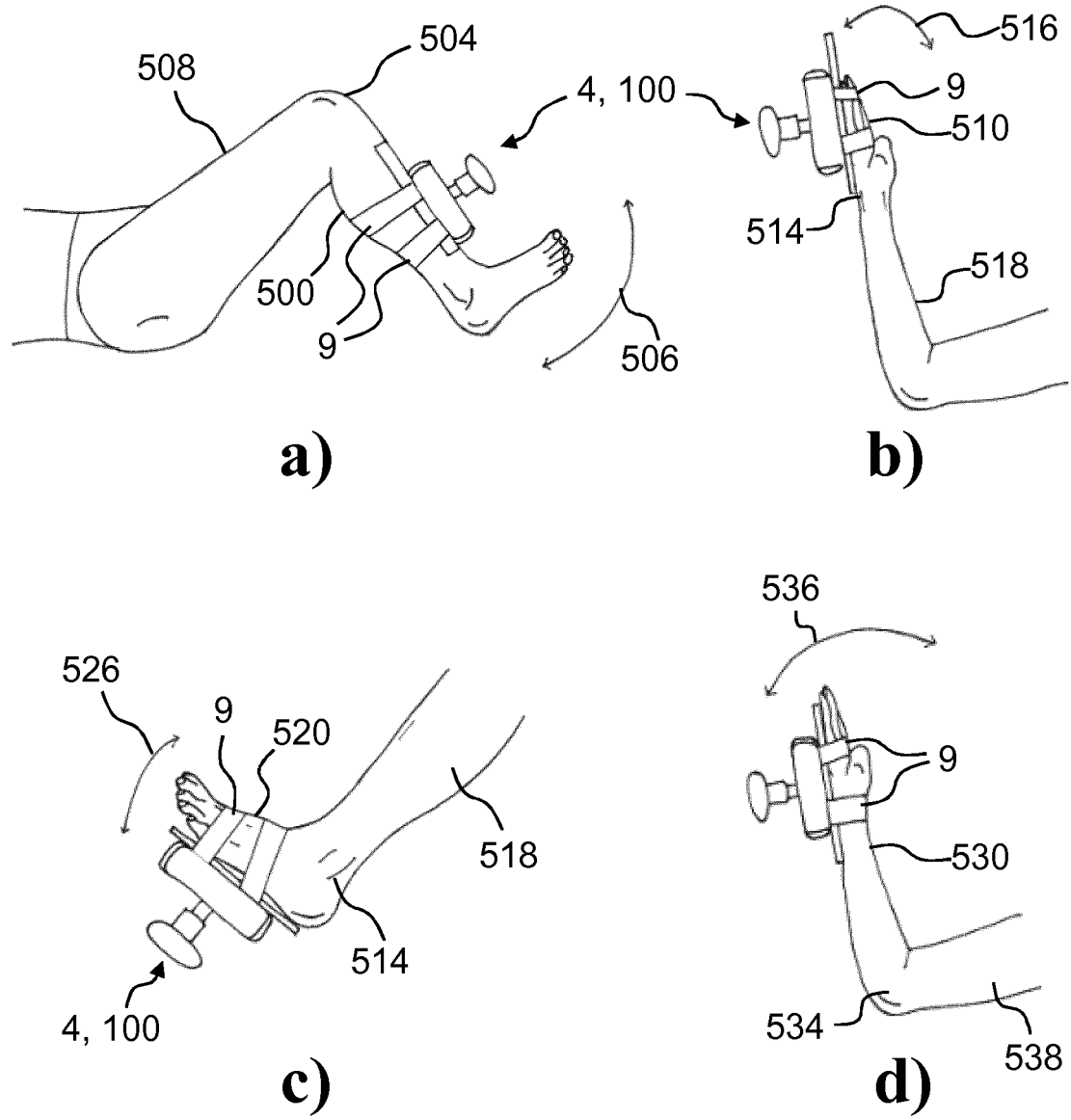
FIGS. 9a-d show exemplary mountings of an exemplary measuring unit or muscle stiffness apparatus.

In an exemplary example of measuring the muscle stiffness in an elbow joint, the measuring unit 4 is applied to the forearm of the subject. Similarly, the muscle stiffness may be measured in other joints. Several exemplary placements or positionings of the measuring unit 4 are depicted in FIG. 9.

The measuring unit 4 may comprise fixating means (9, FIG. 9) for fixating the measuring unit 4 to the body segment. For example, the fixating means may be Velcro straps.

A number of trials are conducted, wherein the subject is asked to relax. A trial consists of an examiner moving the body segment about the joint by applying a force to the subject's body segment. The other body segment of the joint i.e. the body segment proximal to the joint, e.g. the upper arm if the elbow joint is measured, may be fixed by the examiner. A number of trials are conducted, wherein the angular velocity about the joint is varied. The number of trials should include trials with an angular velocity resulting in an elicited stretch reflex, and other trials with an angular velocity that does not result in eliciting of a stretch reflex. Generally an increased angular velocity should increase the likelihood of eliciting a stretch reflex.

It is envisaged that the trials may also be performed automatically or semi-automatically with the use of an arrangement configured to move the selected body segments.

During the number of trials, the measuring device 10 generates a plurality of data sets 12 which are received by the processing unit 6. Each data set of the plurality of data sets comprises data pertaining to one specific trial.

The processing unit 6 analyzes the plurality of data sets 12 for indications of an elicited stretch reflex, and based on this analysis, the plurality of data sets 12 are distributed into two subsets: a first subset comprising data sets having one or more indications of a stretch reflex and another, a second subset, comprising data sets having no indications of a stretch reflex. The processing unit 6 lastly calculates a muscle stiffness score based on differences of stiffness in each subset. Illustrations of an exemplary detection and calculation of a muscle stiffness score is given in relation to FIGS. 7 and 8.

A subset, such as the first subset and/or the second subset, may be an empty subset, e.g. if indications of an elicited stretch reflex are not present in any of the plurality of data sets, the first subset may be an empty subset, and/or if indications of an elicited stretch reflex are present in all of the plurality of data sets, the second subset may be an empty subset.

In such a situation the measuring device 10 and/or the processing unit 6 may be configured to provide an error signal, and/or indicate, e.g. to the examiner, that trials are missing, such as to enable calculation of the muscle stiffness score.

Additionally or alternatively, the measuring device 10 and/or the processing unit 6 may be configured to provide information of an empty first subset and/or second subset, if the first subset is an empty subset and/or if the second subset is an empty subset. The examiner may interpret the provided information of an empty first subset and/or second subset to indicate a physiological situation.

In the example depicted in FIG. 1*b*, the processing unit 6 is provided in a tablet computer, and the processing unit 6 and the measuring unit 4 communicate wirelessly whereby the plurality of data sets 12 are transmitted wirelessly between the measuring unit 4 and the processing unit 6. The wireless communication protocol between the measuring unit 4 and the processing unit 6 may be any wireless protocol, such as Bluetooth and/or Wi-Fi.

In alternative embodiments, the processing unit may be provided in a stationary computer, a laptop computer or a smartphone. It may be beneficial to use a processing unit of a device having a visual display to allow presentation of processed data, i.e. to present the results of the analysis and/or to present measurement data of the analysis.

Figure 2:
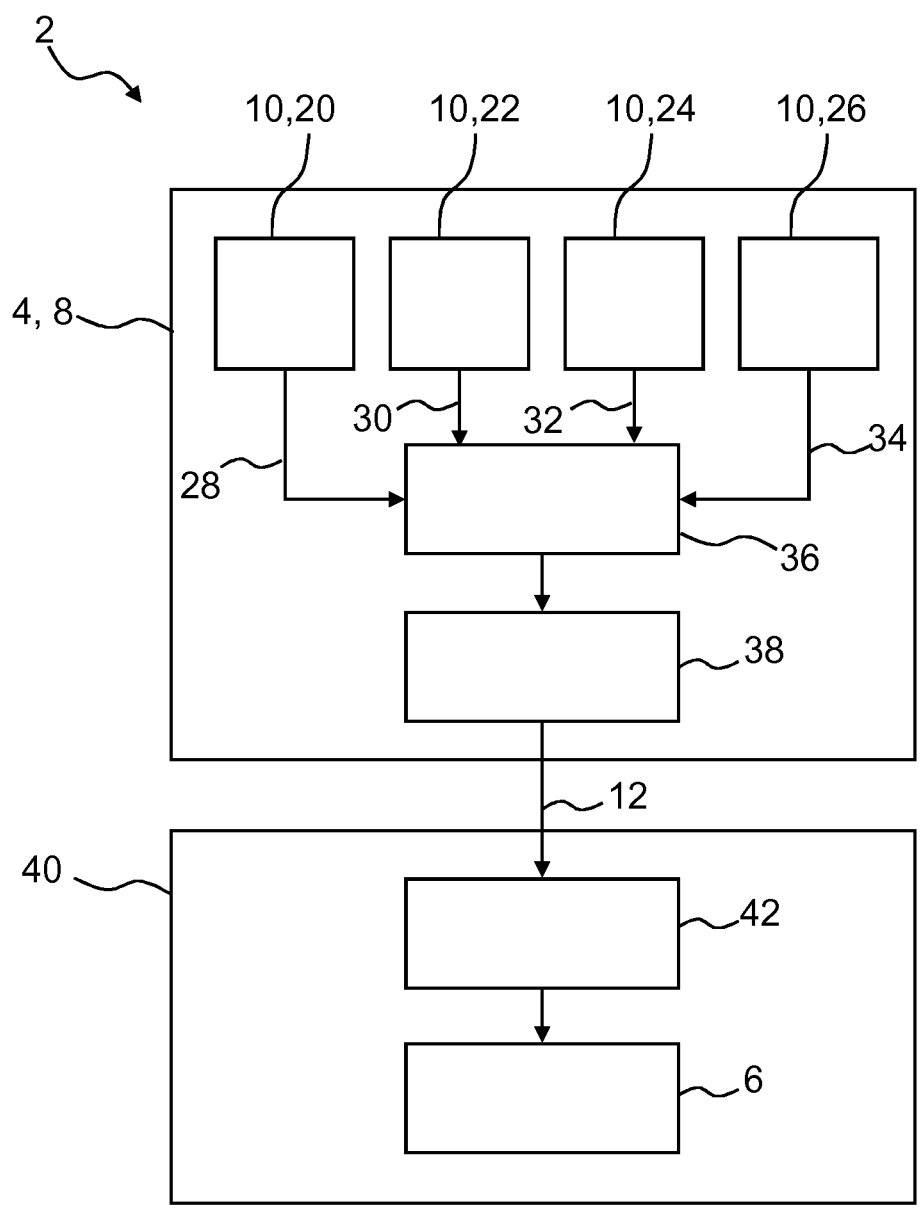

FIG. 2 schematically shows an exemplary system 2 for measuring muscle stiffness in a subject. The exemplary system 2 comprises a measuring unit 4 and an additional device 40 comprising a processing unit 6. The measuring unit 4 and the additional device 40 are here shown as two separate devices.

The measuring unit 4 comprises a housing 8 and a plurality of measurement devices 10. In this particular example, the measuring unit 4 comprises four measurement devices 10 including an accelerometer 20, a gyroscope 22, a force transducer 24 and a muscular activity detection unit 26.

The accelerometer 20 provides acceleration data 28 of the acceleration of the measuring unit 4. The accelerometer 20 may provide acceleration data 28 of acceleration in three directions. The measuring unit 4 is depicted in FIG. 2 with one accelerometer 20. Alternatively, an exemplary measuring unit 4 may comprise a plurality of accelerometers 20 that are positioned in different positions within the measuring unit 4, to provide acceleration data 28 from a plurality of positions within the measuring unit 4.

The gyroscope 22 provides angular velocity data 30 of the measuring unit 4.

The force transducer 24 provides applied force data 32. The body segment is moved by an examiner, while the subject relaxes. The force transducer 24 measures the force applied to the body segment by the examiner.

The muscular activity detection unit 26 provides muscular activity data 34 indicative of muscular activity in a muscle adjacent to joint, e.g. a muscle being stretched during the movement performed by the examiner. The muscular activity detection unit 26 may e.g. be an electromyography unit or a mechanomyography unit. The muscular activity detection unit 26 may detect muscular activity via placement of e.g. surface electrodes on the skin above the muscle. The muscular activity unit 26 may provide muscular activity data 34 of a plurality of muscles.

Measurement data 28, 30, 32, 34 provided by each of the measurement devices 10 forms data sets which are stored in a memory 36 comprised in the measuring unit 4.

The measuring unit 4 further comprises a transmitter 38 for transmitting data sets 12 to the additional device 40. The transmitter 38 receives data sets stored in the memory 36 and transmits these received data sets to the additional device 40. A receiver 42 in the additional device 40 receives the data sets 12 and the data sets 12 are received in the processing unit 6.

The measuring unit 4 may comprise a control unit and/or a processing unit (not shown) to control modules of the measuring unit 4, e.g. the memory 36 and/or the transmitter 38.

In some exemplary systems 2, the transmission of data sets 12 is performed after each trial. Hence, data sets are transmitted one by one. In other exemplary systems 2, a number of trials are performed, and a plurality of data sets is transmitted subsequently.

The data sets 12 from the transmitter 38 to the receiver 42 may be transmitted utilizing a hardwired connection, e.g. in a docking station, or the transmitter 38 and the receiver 42 may be a wireless transmitter and/or transceiver and a wireless receiver and/or transceiver, respectively and the data sets 12 may be transmitted via wireless communication, such as Wi-Fi, Bluetooth, Near Field Communication, NFC, etc.

The transmitter 38 and/or the receiver 42 may be transceivers and provide bidirectional communication. Transmission of data from the additional device 40 to the measuring unit 4 may e.g. be utilized to send commands and/or instructions to the measuring unit 4 i.e. to control the measuring unit 4 by the additional device 40.

In FIG. 2 the measuring unit 4 comprises four different measuring devices 10. However in other exemplary measuring units 4, the measuring devices 10 may include fewer or more measuring devices 10. For example, a measuring unit 4 may comprise two accelerometers 20, two muscular activity detection units 26, or a muscular activity detection unit 26 may be omitted.

The measuring unit 4 may comprise a power supply and/or a battery for powering the components of the measuring unit 4.

Figure 3:
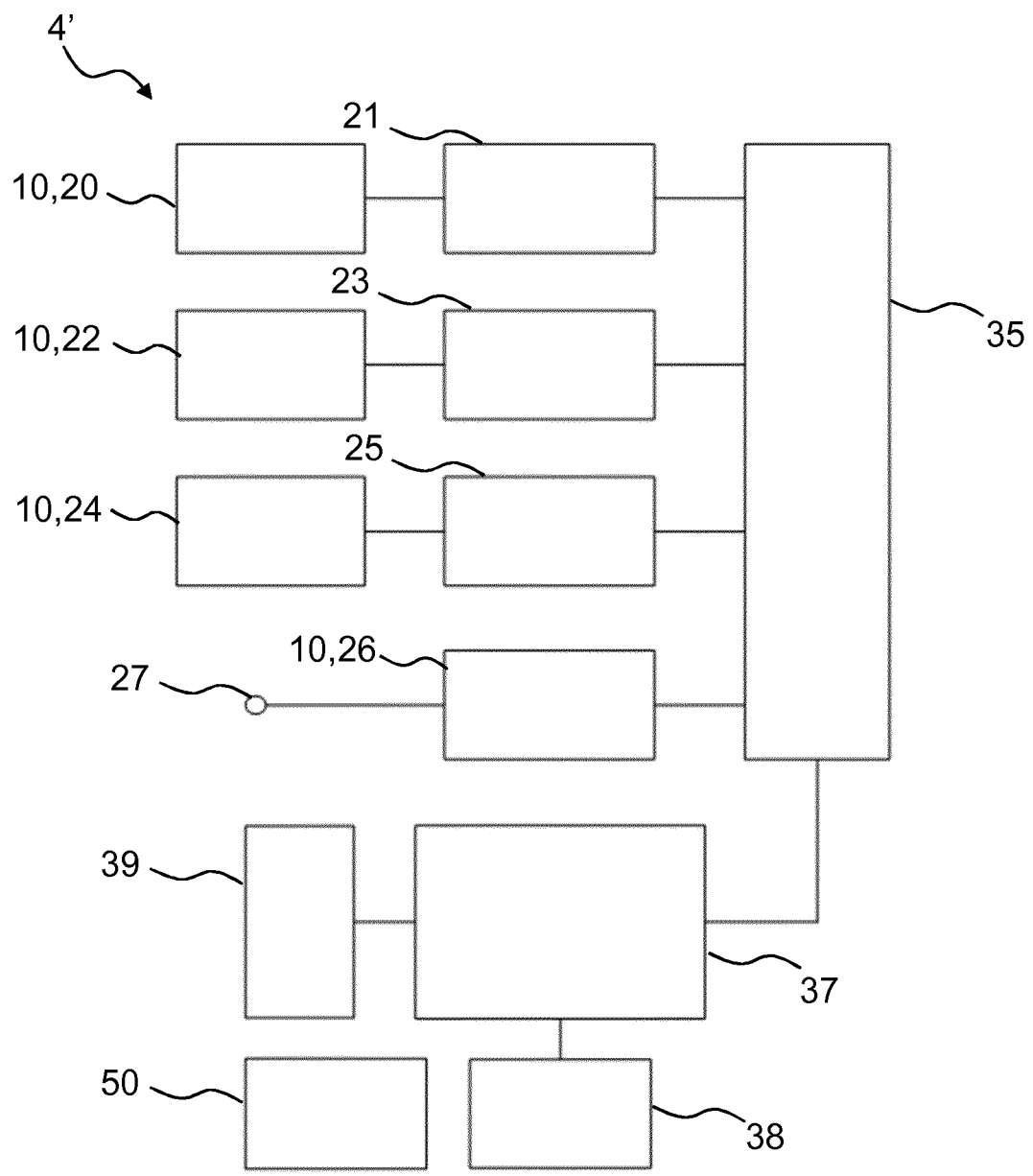

FIG. 3 illustrates a block diagram of an exemplary measuring unit 4'.

The exemplary measuring unit 4' comprises accelerometer(s) 20, gyroscope(s) 22, and force transducer(s) 24. The accelerometer(s) 20, the gyroscope(s) 22, and the force transducer(s) 24 are connected to a first analog preprocessor, a second analog preprocessor and a third analog preprocessor, respectively. The first, second and/or third analog preprocessor may comprise amplifiers and/or filters, e.g. low pass and/or high pass filters.

Furthermore, the exemplary measuring unit 4' comprises a muscular activity unit 26, e.g. an EMG unit, and an electrode connector 27 for connecting external electrodes to the muscular activity unit 26. The muscular activity unit may comprise preprocessing means such as amplifiers and/or filters, e.g. low pass and/or high pass filters.

In an alternative exemplary measuring unit, the first, second and third preprocessors 21, 23, 25 may be incorporated into the corresponding measurement device 10.

The first, second and third preprocessors 21, 23, 25 and the muscular activity unit 26 are connected to an analog to digital converter (ADC) 35. The ADC 35 converts the analog input of each of the measurement devices 10 to a digital representation. The digital output of the ADC 35 is received in a processing module 37. The processing module 37 may comprise a CPU and memory for processing received digital input, such as the digital output of the ADC 35.

The measuring unit 4' furthermore comprises a transceiver 38 for communicating with an additional device (not shown) as described in relation to FIG. 2. The transceiver 38 may be a wireless transceiver such as a radio transceiver. The transceiver 38 is connected to the processing module 37. The processing module 37 may receive a digital signal from the ADC 35 and transmit the signal via the transceiver 38 to an additional device as described in relation to FIG. 2.

The measuring unit 4' furthermore comprises a user interface 39 for interaction with a user of the measuring unit 4'. The user interface 39 may comprise one or more buttons, one or more navigation keys, a visual display and/or one or more speakers. The user interface 39 is connected to the processing module 37. The processing module may provide feedback to the user, and receive input from the user via the user interface 39.

The measuring unit 4' furthermore comprises a power supply unit 50 for powering the circuitry of the measuring unit 4'. The power supply unit 50 may comprise one or more batteries, battery charger circuitry, power-on reset (POR) circuitry, voltage regulators, and/or on/off switches etc.

Figure 4:
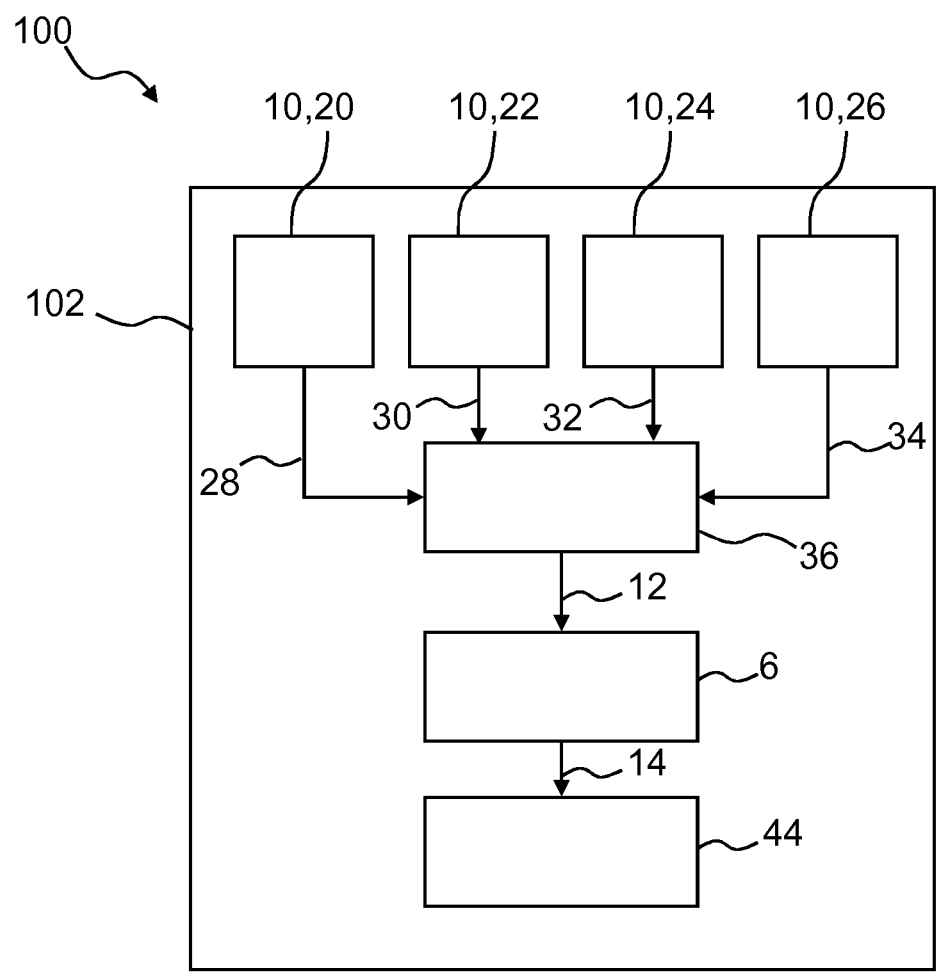

FIG. 4 shows an exemplary muscle stiffness apparatus 100 for measuring muscle stiffness in a joint of a subject. The muscle stiffness apparatus 100 comprises a housing 102 enclosing a plurality of measuring devices 10, memory 36, a processing unit 6 and an output unit 44. The muscle stiffness apparatus 100 is configured to be applied to a body segment e.g. the foot, the lower leg, or the forearm of the subject. The muscle stiffness apparatus 100 is to be applied to the body segment distal to the joint for which the muscle stiffness is to be measured.

The muscle stiffness apparatus 100 may comprise fixating means (not shown) for fixating the muscle stiffness apparatus 100 to the body segment. For example, the fixating means may be Velcro straps.

A number of trials are conducted as described in relation to FIG. 1. During the number of trials, the measuring device(s) 10 generate a plurality of data sets 12 that is received by the processing unit 6. The processing unit 6 analyzes the plurality of data sets 12 for indications of an elicited stretch reflex, and determines two subsets, a first subset comprising data sets with one or more indications of a stretch reflex and another, a second subset, comprising data sets in which no indications of a stretch reflex are present. The processing unit 6 calculates a first stiffness from the data sets of the first subset and a second stiffness from the data sets of the second subset, and calculates a muscle stiffness score 14 based on a difference of stiffness in each subset, such as a difference between the first stiffness and the second stiffness.

The calculated muscle stiffness score 14 is received by the output unit 44. The output unit 44, e.g. visual display, a PC screen, a tablet computer, a smartphone, is configured to present at least the calculated muscle stiffness score 14 to an examiner and/or a user of the muscle stiffness apparatus 100.

The muscle stiffness apparatus 100, as depicted in FIG. 4, comprises a plurality of measuring devices 10 including an accelerometer 20, a gyroscope 22, a force transducer 24 and a muscular activity detection unit 26.

Measurement data 28, 30, 32, 34 provided by each of the measurement devices 10 forms data sets 12 which are stored in the memory 36 and subsequently received by the processing unit 6.

Figure 5:
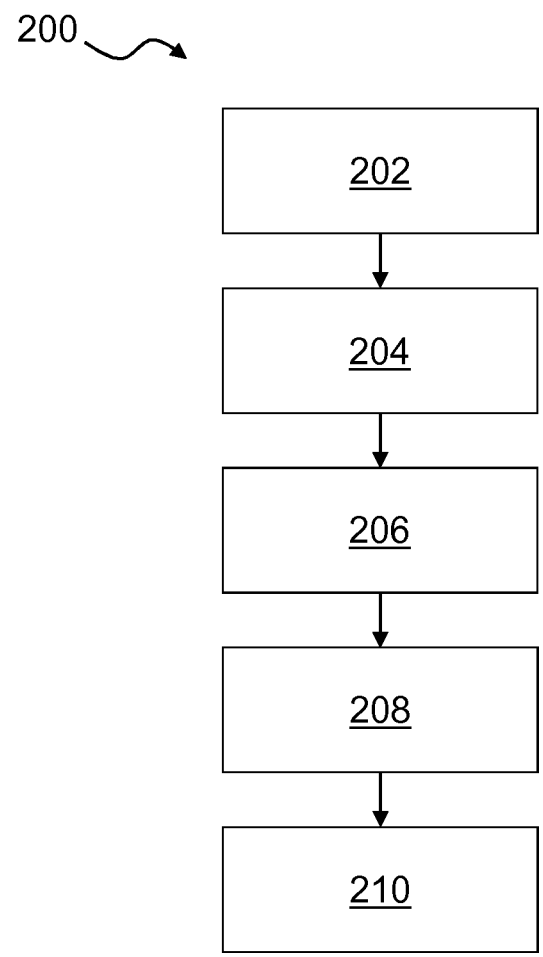
FIG. 5 is flow diagram of a method for calculating a muscle stiffness score.

FIG. 5 shows a flow diagram of an exemplary method 200 for calculating a muscle stiffness score of a joint in a subject. The method 200 comprises applying or attaching at least one measurement device 202, e.g. an accelerometer, a gyroscope, a force transducer, or a muscular activity detection unit, to a body segment distal to the joint. Subsequently, a number of trials are performed 204. Each trial comprises the step of an examiner moving the body segment about the joint while the subject relaxes. Each trial comprises moving the body segment about the joint with an angular velocity. The angular velocity is varied between trials, such that some trials are performed with a slow angular velocity, e.g. slower than 20 deg/s, while others are performed with a fast angular velocity e.g. faster than 200 deg/s.

The method 200 further comprises receiving a plurality of data sets 206 from the at least one measurement device. The plurality of data sets received comprises measurement data measured during the trials. Each data set comprises measurement data of a trial. The step of receiving the data sets 206 may include receiving a data set after each trial, such that the receiving of data sets 206 and performing of trials 204 are performed concurrently.

After receiving the plurality of data sets 206, the method 200 comprises analyzing the plurality of data sets 208. The step of analyzing the plurality of data sets 208 comprises analyzing each data set to determine which, if any, data sets have one or more indications of an elicited stretch reflex. The step of analyzing the plurality of data sets 208 further comprises determining two subsets, a first subset and a second subset, of the plurality of data sets. The first subset comprises data sets of the plurality of data sets, in which at least one of the one or more indications of an elicited stretch reflex is present. Conversely, the second subset comprises data sets of the plurality of data sets, in which none of the one or more indications of an elicited stretch reflex is present.

Analyzing the data sets for one or more indications of an elicited stretch reflex may be based on the measurement data. The one or more indications of an elicited stretch reflex may comprise indications such as muscular activity, increased applied force, a reversal of angular velocity, or any combination hereof.

Figure 6:
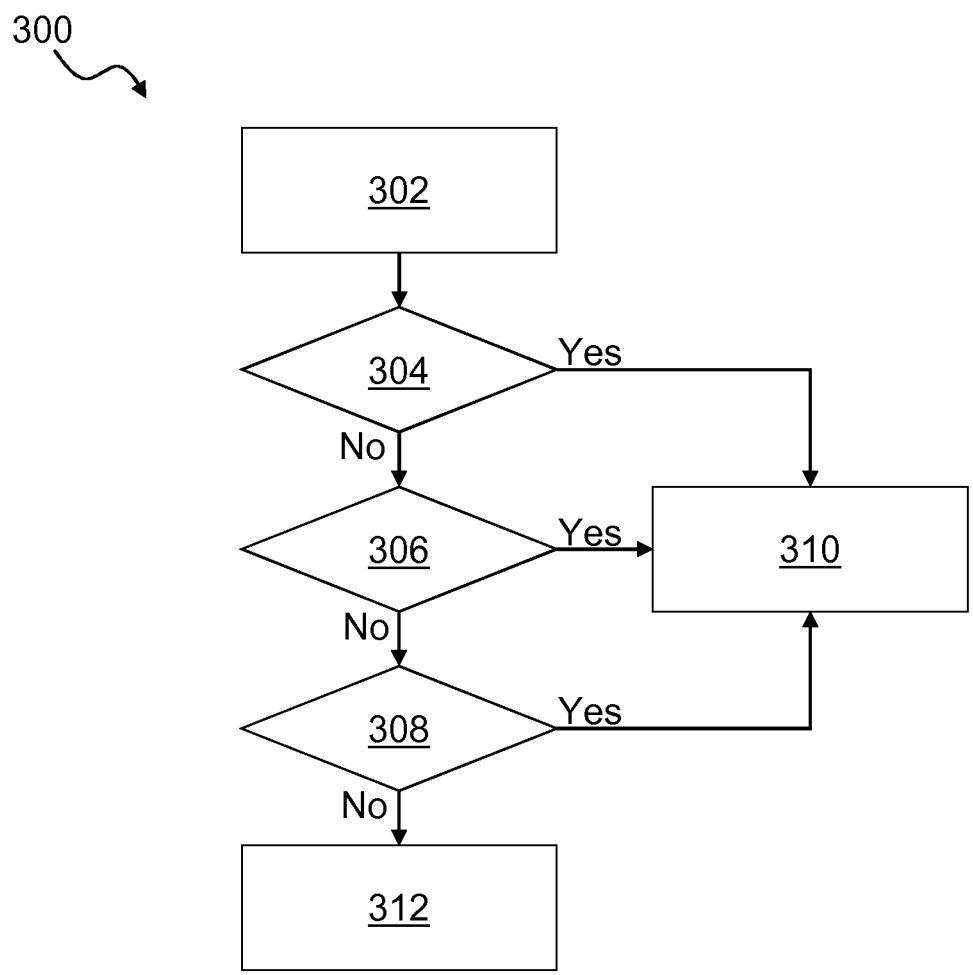
FIG. 6 is a flow diagram of a method for analyzing a data set.

A method of analyzing a data set, in order to form the first subset and the second subset, is described in further detail in relation to FIG. 6.

Subsequently to analyzing the plurality of data sets 208, the method 200 comprises calculating the muscle stiffness score 210. The calculation of the muscle stiffness score 210 is based on a difference between stiffness of the first subset and stiffness of the second subset. A first stiffness is determined from data sets in the first subset, e.g. an average, median, or sum of calculated stiffnesses of data sets in the first subset. Similarly, a second stiffness is determined from data sets in the second subset, e.g. an average, median, or sum of calculated stiffnesses of data sets in the second subset. The resulting muscle stiffness score is calculated based on a difference between the first stiffness and the second stiffness.

The first subset and/or the second subset, may be an empty subset, e.g. if indications of an elicited stretch reflex are not present in any of the plurality of data sets, the first subset may be an empty subset, and/or if indications of an elicited stretch reflex are present in all of the plurality of data sets, the second subset may be an empty subset.

The method may additionally comprise providing an error signal, and/or indicate to the examiner that trials are missing to enable calculation of the muscle stiffness score, and/or provide information of an empty first subset and/or second subset, if the first subset is an empty subset and/or if the second subset is an empty subset.

An examiner may interpret the provided information of an empty first subset and/or second subset to indicate a physiological condition.

The method may be performed by attaching a muscle stiffness apparatus 100 or a measuring unit 4 to a body segment. Thus, the method may comprise the step of attaching a muscle stiffness apparatus 100 or a measuring unit 4 to a body segment.

FIG. 6 is a flow diagram of an exemplary method of analyzing a data set 300 in order to form a first subset and a second subset. The first subset comprising data sets in which at least one of one or more indications of an elicited stretch reflex is present. The second subset comprises data sets in which none of one or more indications of an elicited stretch reflex is present.

The method of analyzing 300 comprises the step 302 of receiving a data set. The data set may be received from a measuring unit, measuring devices, a muscle stiffness apparatus, etc., or the data set may be received from a memory.

The received data set comprises a plurality of data. In the depicted example the data set comprises at least first data, second data, and third data, e.g. angular velocity data, applied force data, and muscular activity data.

After the step of receiving a data set 302, the first data of the data set is analyzed in step 304 for indications of an elicited stretch reflex. If the analysis 304 of the first data reveals indications of an elicited stretch reflex, the data set is allocated to the first subset in step 310.

If the analysis 304 of the first data does not reveal indications of an elicited stretch reflex, the second data of the data set is analyzed in step 306 for indications of an elicited stretch reflex. If the analysis of the second data 306 reveals indications of an elicited stretch reflex, the data set is placed in the first subset 310.

If the analysis of the second data 306 does not reveal indications of an elicited stretch reflex, the third data of the data set is analyzed in step 308 for indications of an elicited stretch reflex. If the analysis of the third data 308 reveals indications of an elicited stretch reflex, the data set is placed in the first subset 310.

If the analysis of the third data 308 does not reveal indications of an elicited stretch reflex, e.g. none of the analyses of the first, second and third data 304, 306, 308 revealed indications of an elicited stretch reflex, the data set is allocated in the second subset 312. Thus, if for example neither the angular velocity data, the applied force data, nor the muscular activity data of a particular data set show signs of an elicited stretch reflex, then the particular data set is allocated to the second subset.

Another exemplary method of analysing data (not shown) may incorporate analysis of any combinations of data to detect an indication of an elicited stretch reflex.

Figure 7:
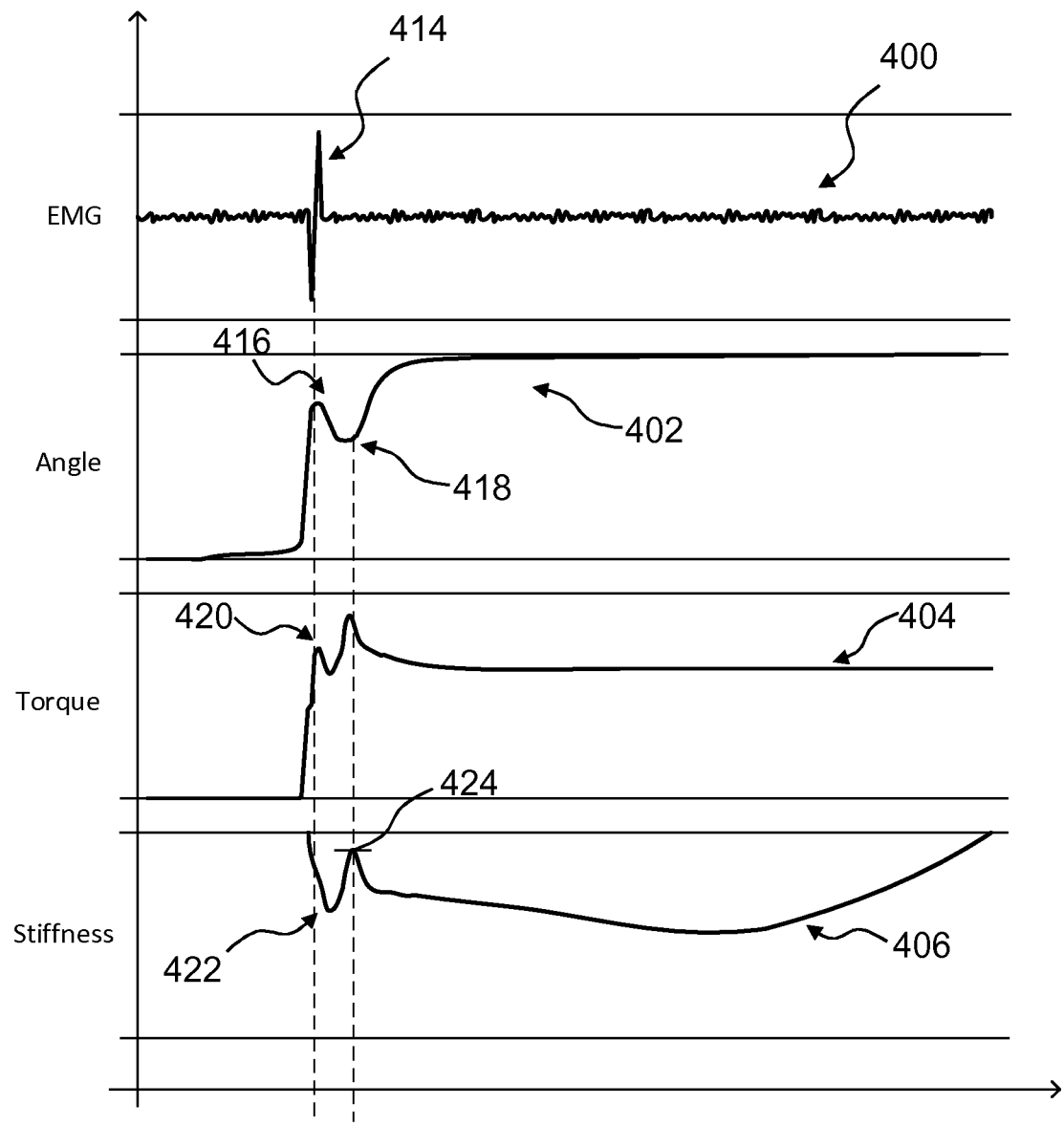
FIG. 7 shows time traces of an exemplary data set during a fast movement.

FIG. 7 shows time traces of an exemplary data set involving a fast movement of the body segment, such as a movement with an angular velocity of more than 200 deg/s., Thus, FIG. 7 shows a trace of muscular activity 400, a trace of angle 402, a trace of applied torque 404, and a trace of a calculated stiffness 406, during the fast movement.

In the depicted example, muscular activity 400 is an EMG signal, the angle 402 is measured relative to a starting position, the torque 404 is measured applied force perpendicular to, and multiplied with, a distance to the joint centre of rotation, and stiffness is calculated as the torque 404 divided by the angle 402.

The fast movement as illustrated by the traces of FIG. 7 shows a stretch reflex being elicited. The elicited stretch reflex is clearly seen as a sudden activity 414 on the muscular activity trace 400. It is seen in this example that the sudden muscle retraction also causes indications seen on the angle trace 416, on the torque trace 420, and on the stiffness trace 422. After detection of the stretch reflex, e.g. from the muscular activity trace 400, the stiffness is analysed to determine a local maximum in a predetermined interval following the detected stretch reflex, such as between 100 and 300 ms after the detected stretch reflex. The determined stiffness maximum 424 may be labelled as the total stiffness. The stiffness maximum 424 is typically found around 200 ms after a stretch reflex detected from muscular activity 414.

The total stiffness may be determined as an average within a predefined window of the determined stiffness maximum 424. For example, the total stiffness may be an average of the stiffness within plus/minus 50 ms of the determined stiffness maximum.

The angle 418 coinciding with the determined stiffness maximum 424 is used to determine a corresponding stiffness during a slow movement.

Figure 8:
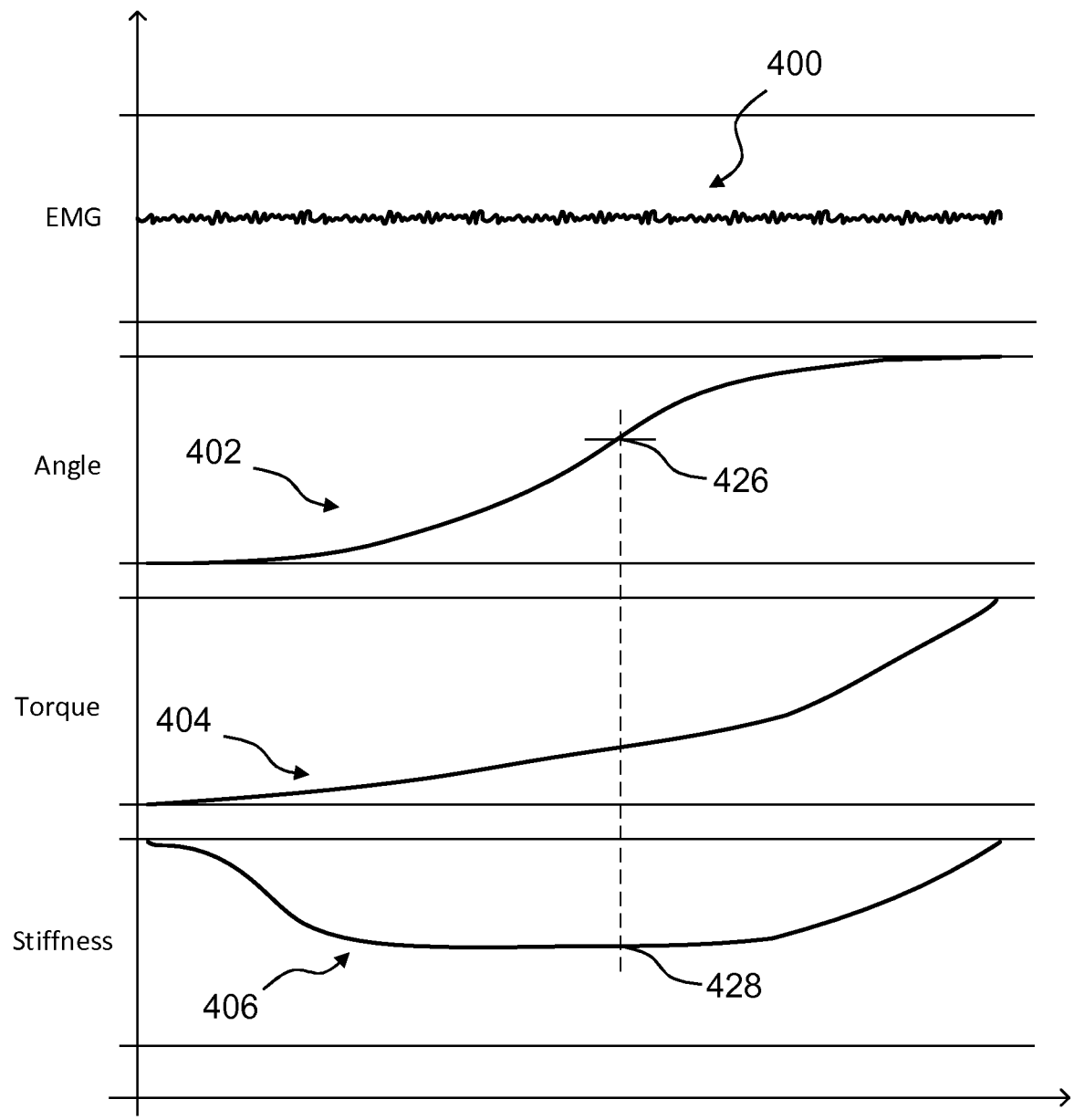
FIG. 8 shows time traces of another exemplary data set during a slow movement.

FIG. 8 shows time traces of another exemplary data set involving a slow movement of the body segment, such as a movement with an angular velocity of less than 20 deg/s. FIG. 8 show a trace of muscular activity 400, a trace of angle 402, a trace of applied torque 404, and a trace of calculated stiffness 406, during the slow movement. The joint measured in relation to FIG. 8 is as measured in relation to FIG. 7. The slow movement does not, in the present example, elicit a stretch reflex. The absence of a stretch reflex is apparent from the traces 400, 402, 404, 406, and e.g. the muscular activity trace 400 shows no indications of sudden muscular activity, and neither does the torque trace 404 show any indications of a sudden increase in torque.

An angle 426 is determined, the angle corresponding to the angle 418 determined during the fast movement as described in relation to FIG. 7. The stiffness 428 coinciding with or corresponding to the angle 426 is the stiffness which may be labelled the passive stiffness. A muscle stiffness score is finally calculated based on the difference between the total stiffness 424 and the passive stiffness 428. For example the muscle stiffness score may be calculated as:

Muscle stiffness score=Total stiffness−Passive stiffness.

The passive stiffness 428 may be determined as an average of measured stiffness values. The average of measured stiffness values may be an average of measured stiffness values between a stiffness value coinciding with a lower boundary angle and a stiffness value coinciding with an upper boundary angle. For example, the lower boundary and the upper boundary may be the angle 426 plus/minus a predetermined upper/lower threshold respectively, e.g. plus/minus 3 degrees or plus/minus 2 degrees. The upper and lower threshold may be different or equal.

FIGS. 9a-d show exemplary mountings of an exemplary measuring unit 4 or an exemplary muscle stiffness apparatus 100.

FIG. 9a shows the measuring unit 4 or the muscle stiffness apparatus 100 applied to a lower leg of a subject. The joint for which a muscle stiffness score is to be measured is the knee joint 504. Hence, the measuring unit/muscle stiffness apparatus 4,100 is applied to the body segment distal to the knee joint, i.e. the shank 500. The measuring unit/muscle stiffness apparatus 4,100 is attached to the shank 500 by fixating means 9. The other body segment proximal to the knee joint 504, i.e. the thigh 508 may be fixed by the examiner.

The examiner is hereafter able to move the shank 500 about the knee joint 504 in either of the directions 506 by either pulling or pushing on the measuring unit/muscle stiffness apparatus 4,100 while the measuring unit/muscle stiffness apparatus 4,100 collects measurement data, such as acceleration data, applied force data, and/or angular velocity data.

FIG. 9b shows the measuring unit 4 or the muscle stiffness apparatus 100 applied to a hand 510 of a subject. The joint for which a muscle stiffness score is to be measured is the wrist 514. Hence, the measuring unit/muscle stiffness apparatus 4,100 is applied to the body segment distal to the wrist 514, i.e. the hand 510. The measuring unit/muscle stiffness apparatus 4,100 is attached to the hand 510 by fixating means 9. The other body segment proximal to the wrist 514, i.e. the forearm 518 may be fixed by the examiner.

The examiner is hereafter able to move the hand 510 about the wrist 514 in either of the directions 516 by either pulling or pushing on the measuring unit/muscle stiffness apparatus 4,100 while the measuring unit/muscle stiffness apparatus 4,100 collects measurement data, such as acceleration data, applied force data, and/or angular velocity data.

FIG. 9c shows the measuring unit 4 or the muscle stiffness apparatus 100 applied to a foot 520 of a subject. The joint for which a muscle stiffness score is to be measured is the ankle 524. Hence, the measuring unit/muscle stiffness apparatus 4,100 is applied to the body segment distal to the ankle 524, i.e. the foot 520. The measuring unit/muscle stiffness apparatus 4,100 is attached to the foot 520 by fixating means 9. The other body segment proximal to the ankle 524, i.e. the shank 528 may be fixed by the examiner.

The examiner is hereafter able to move the foot 520 about the ankle 524 in either of the directions 526 by either pulling or pushing on the measuring unit/muscle stiffness apparatus 4,100 while the measuring unit/muscle stiffness apparatus 4,100 collects measurement data, such as acceleration data, applied force data, and/or angular velocity data.

FIG. 9d shows the measuring unit 4 or the muscle stiffness apparatus 100 applied to a forearm 530 of a subject. The joint for which a muscle stiffness score is to be measured is the elbow joint 534. Hence, the measuring unit/muscle stiffness apparatus 4,100 is applied to the body segment distal to the elbow joint 534, i.e. the forearm 530. The measuring unit/muscle stiffness apparatus 4,100 is attached to the forearm 530 by fixating means 9. The other body segment proximal to the elbow joint 534, i.e. the upper arm 538 may be fixed by the examiner.

The examiner is hereafter able to move the forearm 530 about the elbow joint 534 in either of the directions 536 by either pulling or pushing on the measuring unit/muscle stiffness apparatus 4,100 while the measuring unit/muscle stiffness apparatus 4,100 collects measurement data, such as acceleration data, applied force data, and/or angular velocity data.

Fixating the other body segment, proximal to the joint which is being measured, may be achieved by using a belt or straps, or alternatively the examiner may hold the other body segment against a base surface. Using belts or straps may be beneficial if a joint involving greater muscle such as the knee is examined, whereas the examiner may be able to fixate the other body segment by his weight and/or strength in other cases.

LIST OF REFERENCES 2 system
4 measuring unit
6 processing unit
8 housing
9 fixating means
10 measurement device
12 data sets
14 muscle stiffness score
20 accelerometer
21 first analog preprocessor
22 gyroscope
23 second analog preprocessor
24 force transducer
25 third analog preprocessor
26 muscular activity unit
27 electrode connector
28 acceleration data
30 angular velocity data
32 applied force data
34 muscular activity data
35 analog to digital converter (ADC)
36 memory 37 processing module
38 transmitter/transceiver
39 user interface
40 additional device
42 receiver/transceiver
44 output unit
50 power supply unit
100 muscle stiffness apparatus
102 housing
200 method for calculating muscle stiffness score
202 applying a measurement device
204 perform a number of trials
206 receiving a plurality of data sets
208 analyzing the plurality of data sets
210 calculating the muscle stiffness score
300 method of analyzing a data set
302 receiving a data set
304 analyzing first data
306 analyzing second data
308 analyzing third data
310 put the data set in a first subset
312 put the data set in a second subset
400 exemplary muscular activity trace
402 exemplary angular trace
404 exemplary torque trace
406 exemplary stiffness trace
414 stretch reflex seen on muscular activity trace
416 stretch reflex seen on angle trace
418 angle of maximum stiffness
420 stretch reflex seen on torque trace
422 stretch reflex seen on stiffness trace
424 stiffness maximum/total stiffness
426 angle corresponding to angle of maximum stiffness
428 passive stiffness
500, 510, 520, 530 distal segment
504, 514, 524, 534 joint
506, 516, 526, 536 movement
508, 518, 528, 538 proximal segment

The invention claimed is:

1. A system for measuring muscle stiffness in a predetermined joint of an individual, the system comprising a measuring unit and a processing unit, wherein the measuring unit comprises a wireless transceiver configured to wirelessly communicate with an additional device, wherein the measuring unit is configured to be applied to a body segment of the predetermined joint and comprises a housing and at least one measurement device comprising a force transducer, and wherein the processing unit is configured to:
receive a plurality of data sets from the at least one measurement device, the plurality of data sets comprising measurement data measured during a plurality of trials, the plurality of trials comprising moving the body segment with a plurality of angular velocities by a human examiner other than the individual applying external force to the body segment via the measuring unit, the measurement data comprising applied force data and angular velocity data, wherein the at least one measurement device comprises a gyroscope, wherein annular velocities of the plurality of angular velocities are varied randomly between trials;
analyze the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present;
determine a distance from a joint center of the predetermined joint to a position of the measuring unit;
calculate a muscle stiffness score based on at least a difference between a first stiffness and a second stiffness,
wherein the first stiffness is based on the applied force data and on the determined distance from the joint center of the predetermined joint to the position of the measuring unit, and is determined from the first subset, and
wherein the second stiffness is based on the applied force data and on the determined distance from the joint center of the predetermined joint to the position of the measuring unit, and is determined from the second subset; and
transmit the calculated muscle stiffness score to an output unit to cause the output unit to display the score to a user of the system.

2. The system according to claim 1, wherein the at least one measurement device comprises an accelerometer, and the measurement data comprises acceleration, data.

3. The system according to claim 2, wherein the processing unit calculates acceleration and angular velocity of the measuring unit based on angular velocity data received from the gyroscope and acceleration data received from the accelerometer.

4. The system according to claim 1, wherein the measuring unit comprises a handle, and wherein the force transducer is configured for measuring force applied to the handle.

5. The system according to claim 1, wherein analyzing the plurality of data sets comprises analyzing applied force data of the plurality of data sets.

6. The system according to claim 1, wherein the at least one measurement device comprises a muscular activity detection unit, and the measurement data comprises muscular activity data.

7. The system according to claim 6 wherein analyzing the plurality of data sets comprises analyzing muscular activity data of the plurality of data sets.

8. The system according to claim 1, wherein the plurality of data sets comprises a trial data set and, the processing unit is configured to analyze the trial data set for the one or more indications of an elicited stretch reflex, and the processing unit is configured to output a first signal if the trial data set comprises at least one of the one or more indications of an elicited stretch reflex.

9. The system according to claim 1, wherein the housing comprises the at least one measurement device.

10. The system according to claim 1, wherein the additional device comprises the processing unit.

11. The system according to claim 1, wherein the housing comprises the processing unit.

12. A method for calculating a muscle stiffness score in a joint of an individual, the method comprising:
providing a measuring unit comprising a wireless transceiver configured to wirelessly communicate with an additional device,
receiving a plurality of data sets comprising measurement data measured during a plurality of trials, the plurality of trials comprising moving a body segment with a plurality of angular velocities by a human examiner other than the individual applying external force to the body segment via the measuring unit, the measurement data comprising applied force data and angular velocity data, wherein the measurement unit comprises a gyroscope, wherein angular velocities of the plurality of angular velocities are varied randomly between trials;

analyzing the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present;

determining a distance from a joint center of the joint to a position of the measuring unit;

calculating the muscle stiffness score based on at least a difference between a first stiffness and a second stiffness, wherein the first stiffness is based on applied force data and on the determined distance from the joint center of the joint to the position of the measuring unit, and is determined from the first subset, and wherein the second stiffness is based on applied force data and on the determined distance from the joint center of the joint to the position of the measuring unit, and is determined from the second subset; and transmitting the calculated muscle stiffness score to an output unit to cause the output unit to display the score to a user of the system.

13. The method according to claim 12, wherein analyzing the plurality of data sets comprises at least analyzing force data and/or muscular activity data of the plurality of data sets.

14. A muscle stiffness apparatus for measuring muscle stiffness in a predetermined joint of an individual, comprising:
a housing,
at least one measurement device comprising a force transducer and a wireless transceiver configured to wirelessly communicate with an additional device, and
a processing unit, wherein the processing unit is configured to:
receive a plurality of data sets from the at least one measurement device, the plurality of data sets comprising measurement data measured during a plurality of trials, the plurality of trials comprising moving the body segment with a plurality of angular velocities by a human examiner other than the individual applying external force to the body segment via the muscle stiffness apparatus, the measurement data comprising applied force data and angular velocity data, wherein the at least one measurement device comprises, wherein angular velocities of the plurality of angular velocities are varied randomly between trials,
analyze the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present;
determine a distance from a joint center of the predetermined joint to a position of the measuring unit,
calculate a muscle stiffness score based on at least a difference between a first stiffness and a second stiffness,
wherein the first stiffness is based on applied force data and on the determined distance from the joint center of the predetermined joint to the position of the measuring unit, and is determined from the first subset, and
wherein the second stiffness is based on applied force data and on the determined distance from the joint center of the predetermined joint to the position of the measuring unit, and is determined from the second subset, and
transmit the calculated muscle stiffness score to an output unit to cause the output unit to display the score to a user of the system, and
wherein the muscle stiffness apparatus is configured to be applied to a body segment of the predetermined joint.

15. A system for measuring muscle stiffness in a predetermined joint of an individual, the system comprising a measuring unit and a processing unit, the measuring unit being configured to be applied to a body segment of the predetermined joint and comprising a housing and at least one measurement device comprising a force transducer, wherein the housing comprises the processing unit, and wherein the processing unit is configured to:
receive a plurality of data sets from the at least one measurement device, the plurality of data sets comprising measurement data measured during a plurality of trials, the plurality of trials comprising moving the body segment with a plurality of angular velocities by a human examiner other than the individual applying external force to the body segment via the measuring unit, the measurement data comprising applied force data and angular velocity data, wherein the at least one measurement device comprises a gyroscope, wherein angular velocities of the plurality of angular velocities are varied randomly between trials;
analyze the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present;
determine a distance from a joint center of the predetermined joint to a position of the measuring unit;
calculate a muscle stiffness score based on at least a difference between a first stiffness and a second stiffness,
wherein the first stiffness is based on the applied force data and on the determined distance from the joint center of the predetermined joint to the position of the measuring unit, and is determined from the first subset, and
wherein the second stiffness is based on applied force data and on the determined distance from the joint center of the predetermined joint to the position of the measuring unit, and is determined from the second subset; and
transmit the calculated muscle stiffness score to an output unit to cause the output unit to display the score to a user of the system.

16. A method for calculating a muscle stiffness score in a joint of an individual, the method comprising:
    receiving a plurality of data sets comprising measurement data measured during a plurality of trials, the plurality of trials comprising moving a body segment with a plurality of angular velocities by a human examiner other than the individual applying external force to the body segment via a measuring unit, the measurement data comprising applied force data and angular velocity data, wherein the measurement unit comprises a gyroscope, wherein angular velocities of the plurality of angular velocities are varied randomly between trials;
    analyzing the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present;
    determining a distance from a joint center of the joint to a position of the measuring unit;
    calculating, via a processing unit, the muscle stiffness score based on at least a difference between a first stiffness and a second stiffness,
    wherein the first stiffness is based on applied force data and on the determined distance from the joint center of the joint to the position of the measuring unit, and is determined from the first subset, and
    wherein the second stiffness is based on applied force data and on the determined distance from the joint center of the joint to the position of the measuring unit, and is determined from the second subset, and wherein a housing comprises the processing unit; and
    transmitting the calculated muscle stiffness score to an output unit to cause the output unit to display the score to a user of the system.

17. A muscle stiffness apparatus for measuring muscle stiffness in a predetermined joint of an individual, comprising:
    a housing comprising a processing unit, and
    at least one measurement device comprising a force transducer,
    wherein the processing unit is configured to:
        receive a plurality of data sets from the at least one measurement device, the plurality of data sets comprising measurement data measured during a plurality of trials, the plurality of trials comprising moving the body segment with a plurality of angular velocities by a human examiner other than the individual applying external force to the body segment via the muscle stiffness apparatus, the measurement data comprising applied force data and angular velocity data, wherein the at least one measurement device comprises a gyroscope, wherein angular velocities of the plurality of angular velocities are varied randomly between trials,
        analyze the plurality of data sets for one or more indications of an elicited stretch reflex based on the measurement data, to determine a first subset and a second subset of the plurality of data sets, the first subset comprising data sets in which at least one of the one or more indications of an elicited stretch reflex is present, and the second subset comprising data sets in which none of the one or more indications of an elicited stretch reflex is present,
        determine a distance from a joint center of the predetermined joint to a position of the measuring unit,
        calculate a muscle stiffness score based on at least a difference between a first stiffness and a second stiffness,
        wherein the first stiffness is based on applied force data and on the determined distance from the joint center of the redetermined joint to the position of the measuring unit, and is determined from the first subset, and
        wherein the second stiffness is based on applied force data and on the determined distance from the joint center of the predetermined joint to the Position of the measuring unit, and is determined from the second subset, and
        transmit the calculated muscle stiffness score to an output unit to cause the output unit to display the score to a user of the system, and
        wherein the muscle stiffness apparatus is configured to be applied to a body segment of the predetermined joint.

* * * * *